United States Patent
Dong et al.

(10) Patent No.: US 10,653,589 B2
(45) Date of Patent: May 19, 2020

(54) PERSONAL CARE COMPOSITION

(71) Applicant: Conopco, Inc., Englewood Cliffs, NJ (US)

(72) Inventors: Wenyan Dong, Shanghai (CN); Naresh Dhirajlal Ghatlia, Bangalore (IN); Lin Wang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/461,038

(22) PCT Filed: Oct. 31, 2017

(86) PCT No.: PCT/EP2017/077905
§ 371 (c)(1),
(2) Date: May 15, 2019

(87) PCT Pub. No.: WO2018/095704
PCT Pub. Date: May 31, 2018

(65) Prior Publication Data
US 2019/0307655 A1  Oct. 10, 2019

(30) Foreign Application Priority Data

Nov. 23, 2016 (CN) .................. PCT/CN2016/106975
Dec. 14, 2016 (EP) ..................................... 16203968

(51) Int. Cl.
| | | |
|---|---|---|
| *A61K 8/04* | (2006.01) | |
| *A61K 8/06* | (2006.01) | |
| *A61K 8/19* | (2006.01) | |
| *A61K 8/81* | (2006.01) | |
| *A61Q 1/02* | (2006.01) | |
| *A61Q 19/08* | (2006.01) | |

(52) U.S. Cl.
CPC .............. *A61K 8/044* (2013.01); *A61K 8/062* (2013.01); *A61K 8/19* (2013.01); *A61K 8/8105* (2013.01); *A61K 8/8111* (2013.01); *A61Q 1/02* (2013.01); *A61Q 19/08* (2013.01); *A61K 2800/26* (2013.01); *A61K 2800/412* (2013.01); *A61K 2800/43* (2013.01); *A61K 2800/592* (2013.01)

(58) Field of Classification Search
CPC .... A61Q 19/08; A61Q 1/02; A61K 2800/592; A61K 8/19; A61K 8/8105; A61K 8/8111
See application file for complete search history.

(56) References Cited

U.S. PATENT DOCUMENTS

| | | |
|---|---|---|
| 5,356,617 A | 10/1994 | Schlossman |
| 7,078,046 B1 | 7/2006 | Rabe et al. |
| 2002/0192252 A1 | 12/2002 | Yen et al. |
| 2003/0113357 A1 | 1/2003 | Hu et al. |
| 2005/0002976 A1 | 1/2005 | Wu |
| 2005/0187128 A1 | 8/2005 | Martin et al. |
| 2007/0207102 A1 | 3/2007 | Student et al. |
| 2009/0081316 A1 | 3/2009 | Wahl et al. |
| 2014/0010769 A1 | 1/2014 | Lomakin et al. |
| 2015/0098973 A1 | 4/2015 | Brissette et al. |
| 2015/0320648 A1 | 11/2015 | Pierre et al. |
| 2016/0067157 A1 | 3/2016 | Brown et al. |

FOREIGN PATENT DOCUMENTS

| | | |
|---|---|---|
| DE | 102005063063 | 10/2006 |
| EP | 1769786 | 2/2010 |
| FR | 2869796 | 11/2005 |
| FR | 2992172 | 12/2013 |
| JP | 2009292772 | 12/2009 |
| KR | 20100048737 | 5/2010 |
| WO | WO0112137 | 2/2001 |
| WO | WO02056846 | 7/2002 |
| WO | WO2014010098 | 1/2014 |
| WO | WO2014111833 | 7/2014 |
| WO | WO2014203913 | 12/2014 |
| WO | WO2016012513 | 1/2016 |
| WO | WO2016149917 | 9/2016 |

OTHER PUBLICATIONS

Momentive; Softouch CC6097 Technical Data Sheet; Momentive; Mar. 13, 2015; pp. 1-3; XP055345274.
Zelens; Youth Glow Foundation; Mintel; Nov. 1, 2014; pp. 1-5; XP002767292.
UNEP; Plastics in Cosmetics; UNEP; Jan. 1, 2015; pp. 1-3; XP005345749.
Avon; Illuminating Day Cream SPF 15; Mintel; Jul. 1, 2012; pp. 1-3; XP002767291.
Dow; OptiTouch Optical and Sensory Additive Frequently Asked Questions; Dow; Nov. 1, 2015; pp. 1-4; XP055345244.
Search Report and Written Opinion in PCTEP2017077905; dated Dec. 19, 2017.
Search Report & Written Opinion in EP16203968; dated Mar. 3, 2017.

*Primary Examiner* — Kortney L. Klinkel
(74) *Attorney, Agent, or Firm* — Ellen Plotkin

(57) ABSTRACT

Disclosed is a personal care composition comprising boron nitride in combination with a non-silicone polyolefin particle in a cosmetically acceptable carrier to provide benefits of enhanced skin appearance.

12 Claims, No Drawings

PERSONAL CARE COMPOSITION

FIELD OF THE INVENTION

The present invention relates to a personal care composition. In particular, the personal care composition is directed to providing enhanced skin appearance like improved blurring, and reduced shine. This is achieved by including turbostratic boron nitride particles in combination with specific polyolefin particles in a personal care composition.

BACKGROUND OF THE INVENTION

Ageing brings with it many changes to the appearance of skin. Of particular concern to individuals wishing to maintain a youthful appearance, is the reduction or elimination of skin imperfections such as wrinkles, age spots or general unevenness of skin tone. Another preferred skin attribute is that of reduced shine. A shiny skin is indicative of oiliness which is an attribute disliked by many consumers. Most people prefer a matte appearance of their skin.

There has been considerable effort by the cosmetics industry to provide compositions which can mask or at least reduce skin imperfections. Often this is achieved by using materials such as talc, silica, kaolin and other inorganic particulates. These inorganic particulates achieve a matte effect due to their optical properties.

An alternative approach is referred to as achieving blurring effect. Here, the incoming light is distorted by scattering (lensing). Components of the cosmetic composition in this mechanism operate as lenses to bend and twist light in a variety of directions.

Traditional approaches, unfortunately, either hide imperfections in the absence of radiance or result in radiance and healthy glow but with aesthetically displeasing skin appearance, for example, through enhanced visibility of skin topography.

The present inventors have recognised that there remains a need to provide a composition which is capable of giving better blurring effect to skin, while ensuring reduced shiny appearance. Therefore, after extensive experimentation, they developed a personal care composition comprising turbostratic boron nitride particles in combination with non-silicone polyolefin particles of specific size in a cosmetically acceptable carrier, which has a higher blurring efficacy.

US2016067157 (Avon) discloses a method of instantly reducing the appearance of wrinkles and skin imperfections while smoothing the skin, which comprises applying a cosmetic composition comprising a fractal particle based gel.

US2002192252 (Procter & Gamble) relates to substantially uniform, discontinuous films of a skin care product having a defined average particle size, particle spacing and coverage value. The films provide improved skin appearance, e.g., good apparent coverage and a natural look. The present inventors have tried the combination of boron nitride and ethylene acrylate copolymer disclosed in this publication and determined that the blurring efficacy of the present invention is substantially better than can be obtained using this combination.

It is thus an object of the present invention to provide for a personal care composition which provides for improved skin appearance by way of enhanced blurring.

SUMMARY OF THE INVENTION

In a first aspect, the present invention provides a personal care composition comprising:
a) turbostratic boron nitride particles;
b) non-silicone polyolefin particles having an average particle size in the range of 0.5 to 5 microns; and
c) a cosmetically acceptable carrier.

In a second aspect, the present invention provides a method of improving the appearance of skin by delivering improved blurring and reduced shine comprising the step of applying a composition of the present invention on the desired skin surface.

In a third aspect, the present invention provides use of composition of the present invention for reducing the appearance of fine lines, wrinkles, pores and/or blemish spots; evening skin tone, or a combination thereof on the desired skin surface.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The disclosure of the invention as found herein is to be considered to cover all embodiments as found in the claims as being multiply dependent upon each other irrespective of the fact that claims may be found without multiple dependency or redundancy.

By "A Personal Care Composition" as used herein, is meant to include a composition for topical application to the skin of mammals, especially humans. Such a composition may be generally classified as leave-on or rinse off but is preferably of the leave on type. The composition is formulated into a product which is applied to a human body specifically for improving appearance but may also be capable of providing cleansing, odor control or general aesthetics. The composition of the present invention can be in the form of a liquid, lotion, cream, foam, scrub, gel, or toner, or applied with an implement or via a face mask or a pad. Non-limiting examples of such compositions include leave-on skin lotions, creams, antiperspirants, deodorants, lipsticks, foundations, mascara, sunless tanners and sunscreen lotions. The composition of the present invention is preferably a leave-on composition. "Skin" as used herein is meant to include skin on the face and body (e.g., neck, chest, back, arms, underarms, hands, legs, buttocks and scalp) and especially to the sun exposed parts thereof.

"Turbostratic boron nitride (t-BN)" as used herein refers to boron nitride having oxygen impurity in the boron nitride crystal lattice.

"Non-silicone polyolefin" particles as used herein refers to polymers of olefins which are substantially free of silicone monomers and are in particulate form.

"Specific surface area" as used herein refers to specific surface area determined according to Brunauer-Emmett-Teller method. The value of the specific surface area is measured by meeting the requirements set out in ASTM standard D 3663-78.

"Average particle size" as used herein refers to the particle size in non-aggregated state unless otherwise stated. The average particle size, as per the present invention is apparent volume median diameter ($d_{50}$, also known as x50 or sometimes d(0.5) of the particles measurable for example, by laser diffraction using a system such as a Mastersizer™ 2000 available from Malvern Instruments Ltd) meeting the requirements set out in ISO 13320 unless otherwise stated. The $d_{10}$ value denotes that 10% of the particles in the sample are below that particle size. $d_{90}$ value denotes that 90% of the particles in the sample are below that particle size.

Boron nitride (BN) is a chemically inert non-oxide ceramic material, which exists in several crystalline varieties, including cubic structure BN (c-BN) analogous to diamond, and hexagonal structure BN (h-BN) analogous to graphite [reference: *Journal of Materials Science & Technology*, Volume 31, Issue 6: 589-598; US2012058342]. In particular, h-BN is widely used in personal care products to which they impart a number of advantageous properties, such as softness, adherence, coverage and a natural look due to their layer-by-layer structure and medium reflectance. Furthermore, according to uniformity of hexagonal crystal structure level, there are different types of h-BN, i.e. graphitic, turbostratic and quasigraphitic 1) Graphitic BN (g-BN) is the purest BN crystals where all the hexagonal BN crystals are aligned parallel with each other.
2) Turbostratic BN (t-BN) has oxygen impurity in the BN crystal lattice. Some of the nitrogen (typically <2%) are replaced with oxygen. Presence of Oxygen distorts the crystal stacking and the planes of BN are not exactly parallel to each other like in case of graphitic BN. These turbostratic BN crystals gives matte effect as there is less specular reflection from them.
3) Quasi graphitic BN is somewhere in between these two morphologies.

The boron nitride for use in the present invention is preferably turbostratic boron nitride. Typically, the turbostratic boron nitride has an average particle size in the range of 100 nm to 10 microns. Preferably the particle size of non-aggregated particles (as measured using SEM) is in the range of 100 nm to 1 micrometer. The particles usually aggregate when stored and the average particle size when measured as aggregates using a technique like dynamic light scattering (DLS) is preferably in the range of 0.5 to 15 microns, more preferably in the range of 3 to 12 microns, and most preferably in the range of 4 to 9 microns.

The specific surface area of the turbostratic boron nitride is preferably from 5 to 80 $m^2/g$, more preferably from 10 to 60 $m^2/g$ and even more preferably from 15 to 40 $m^2/g$. As per especially preferred aspects, the specific surface area of the turbostratic boron nitride is at least 10 $m^2/g$, more preferably at least 20 $m^2/g$, further more preferably at least 25 $m^2/g$.

The content of oxygen in the turbostratic boron nitride is preferably at least 0.2% by mole of the turbostratic boron nitride, more preferably from 0.5 to 3%, even more preferably from 1 to 2%, and most preferably from 1.2 to 1.8% by mole of the turbostratic boron nitride.

The turbostratic boron nitride used in the present invention typically has a tap density ranging from 0.1 $g/cm^3$ to 1 $g/cm^3$ and more preferably from 0.2 $g/cm^3$ to 0.6 $g/cm^3$. Tap density, as used herein, refers to a measure of the density of a powder. The value of tap density refers to the values measured in conformity with international standard ISO 787-11.

Particularly preferred turbostratic boron nitride is Softouch* Boron Nitride Powder CC6097 from Momentive.

For sake of better blurring of the skin, the turbostratic boron nitride is preferably present in amount of 0.1 to 15% by weight of the composition, more preferably 0.1 to 12%, even more preferably from 0.4 to 8%, still even more preferably from 1 to 5% and most preferably from 2 to 4% by weight of the composition.

The composition of the invention comprises non-silicone polyolefin particles in the average size range of 0.5 to 5 microns, preferably 1.1 to 3.3 microns. It is preferred that the polyolefin particles have a $d_{10}$ value higher than 1.1 μm and a $d_{90}$ value lower than 3.3 μm. The polyolefin particles are preferably homo or co-polymers, preferably co-polymers of hydrocarbons having 2 to 10 carbon atoms. The polyolefin preferably does not comprise an oxygen, a silicon or a nitrogen atom in its structure. Further preferably, the polymer does not comprise acrylate in its structure. Preferred olefins that are polymerized to prepare the polymers include ethylene, propylene, octene or combinations thereof. The most preferred non-silicone polyolefin is an ethylene/octene copolymer sufficiently polymerized to be in the particulate form. These polyolefin particles are commercially available as Optitouch™ from Dow chemicals. The polyolefin particles preferably have a refractive index in the range of 1.4 to 1.6 preferably 1.45 to 1.55.

The non-silicone polyolefin particles are preferably included at 0.1 to 10%, more preferably 0.1 to 5% by weight of the composition.

In order to achieve better blurring effect and/or opacity, the weight ratio of the boron nitride to the non-silicone polyolefin particles is preferably from 1:10 to 10:1, more preferably from 1:1 to 4:1.

The composition may additionally comprise other particulate actives like silica and/or silicone elastomer to further enhance the blurring efficacy. Silica particle, if included, is preferably porous silica and is preferably non-fumed silica. Preferably, the porous silica is hydrophilic. The porous silica preferably has an average diameter of 200 nm to 40 microns, more preferably from 0.6 to 25 microns, even more preferably from 1 to 20 microns, still even more preferably from 1.5 to 12 microns and most preferably from 2 to 5 microns. Particularly preferred porous silica includes MSS-500/3H, MSS-500/H from Kobo Products Inc. The porous silica, if included, is preferably present in amount of 0.01 to 20% by weight of the composition, more preferably from 0.05 to 14%, even more preferably from 0.2 to 9%, still even more preferably from 0.4 to 5% and most preferably from 0.8 to 4% by weight of the composition.

The composition may optionally additionally comprise a silicone elastomer. The silicone elastomer used in the present invention is preferably powder of silicone elastomer. It is highly preferred that the silicone elastomer is crosslinked. Preferred silicone elastomers are organo-polysiloxanes available under the INCI names of dimethicone/vinyl dimethicone crosspolymer, dimethicone crosspolymer and Polysilicone-11. More preferably the silicone elastomer is dimethicone/vinyl dimethicone crosspolymer.

Typically, the average diameter of the silicone elastomer is from 0.2 to 50 microns, more preferably from 0.5 to 20 microns, even more preferably from 0.8 to 10 microns, and still even more preferably from 1.5 to 6 microns.

The silicone elastomer is preferably present in amount of 0.5 to 20%, more preferably 1 to 15%, even more preferably from 3 to 12%, still even more preferably from 4.5 to 9 by weight of the composition.

Preferably, the composition additionally comprises a whitening pigment. The whitening pigment are typically particles of high refractive index materials. For example the whitening pigment may have a refractive index of greater than 1.3, more preferably greater than 1.8 and most preferably from 2.0 to 2.7. Examples of such whitening pigment are those comprising bismuth oxy-chloride barium sulfate, mica, silica, titanium dioxide, zirconium oxide, aluminum oxide, zinc oxide or combinations thereof. More preferred whitening pigment are particles comprising titanium dioxide, zinc oxide, zirconium oxide, mica, iron oxide or a combination thereof. Even more preferred whitening pigment are particles comprising zinc oxide, zirconium oxide, titanium dioxide or a combination thereof as these materials have especially high refractive index. Still even more preferably the whitening pigment is selected from titanium dioxide, zinc oxide or a mixture thereof and most preferred whitening pigment is titanium dioxide.

The average diameter of whitening pigment is typical from 15 nm to 2 microns, more preferably from 35 nm to 800 nm, even more preferably from 50 nm to 500 nm and still even more preferably from 100 to 300 nm. Diameter of whitening pigment refers to the diameter of particles in an un-aggregated state. In the event a well-defined sphere is not generated, diameter means the largest measureable distance on a particle The average diameter may be measured for example by scanning electron microscopy (SEM) or transmission electron microscopy (TEM) by averaging the value of at least one hundred particles.

Preferably the composition comprises whitening pigment in an amount of from 0.001 to 10 wt %, more preferably 0.01 to 6 wt %, more preferably still 0.1 to 3 wt % and most preferably 0.2 to 2 wt %.

The composition preferably additionally comprises one or more organic sunscreens. A wide variety of organic sunscreen is suitable for use in combination with the essential ingredients of this invention. Suitable UV-A/UV-B sunscreen include, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. The most suitable organic sunscreens are 2-ethylhexyl-p-methoxycinnamate, butylmethoxydibenzoylmethane or a mixture thereof.

A safe and effective amount of organic sunscreen may be used in the compositions useful in the subject invention. The composition preferably comprises from 0.1% to 10%, more preferably from 0.1% to 5%, of organic sunscreen.

The composition of the invention preferably comprises a skin lightening agent. Vitamin B3 compounds (including derivatives of vitamin B3) e.g. niacin, nicotinic acid or niacinamide are the preferred skin lightening agent as per the invention, most preferred being niacinamide. Vitamin B3 compounds, when used, are preferably present in an amount in the range of 0.1 to 10%, more preferably 0.2 to 5% by weight of the composition.

The composition may comprise other beneficial skin care actives like retinol, retinyl esters, resorcinol, allantoin, ubiquinone, conjugated linoleic acid, 12-hydroxystearic acid or derivatives thereof. Of these the most preferred ones for inclusion in the composition of the invention are anti-aging actives like retinol or retinyl esters.

Compositions of the present invention will also include a cosmetically acceptable carrier. In some embodiments the carrier will be (or at least comprise) a water and oil emulsion, which in certain embodiments may be water-in-oil emulsion. Preferred emulsions, however, are the oil-in-water variety.

Preferred hydrophobic material for use in the oil phase of such emulsions includes emollients such as fats, oils, fatty alcohols, fatty acids, soaps, silicone oils, synthetic esters and/or hydrocarbons.

Silicones may be divided into the volatile and nonvolatile variety. Volatile silicone oils (if used) are preferably chosen from cyclic (cyclomethicone) or linear polydimethylsiloxanes containing from 3 to 9, preferably from 4 to 5, silicon atoms.

Nonvolatile silicones useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m$^2$/s at 25° C. Among the preferred nonvolatile emollients useful in the present compositions are the polydimethyl siloxanes having viscosities from about $1 \times 10^{-s}$ to about $4 \times 10^{-4}$ m$^2$/s at 25° C.

Specific examples of non-silicone emollients include stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate, and mixtures thereof.

Among the ester emollients are:

a) Alkenyl or alkyl esters of fatty acids having 10 to 20 carbon atoms. Examples thereof include isoarachidyl neopentanoate, isodecyl neopentanoate, isononyl isonanoate, cetyl ricinoleate, oleyl myristate, oleyl stearate, and oleyl oleate;

b) Ether-esters such as fatty acid esters of ethoxylated fatty alcohols;

c) Polyhydric alcohol esters. Butylene glycol, ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols. An Example is pentaerythrityl tetraethylhexanoate;

d) Wax esters such as beeswax, spermaceti wax and tribehenin wax;

e) Sterols esters, of which cholesterol fatty acid esters are examples thereof;

f) Sugar ester of fatty acids such as sucrose polybehenate and sucrose polycottonseedate; or g) mixtures of two or more of the foregoing (a) to (f).

Of particular use also are the $C_{12-15}$ alkyl benzoate esters sold under the Finsolve brand.

Hydrocarbons which are suitable emollients include petrolatum, mineral oil, $C_{11}$-$C_{13}$ isoparaffins, polyalphaolefins, isohexadecane or a mixture thereof.

Amounts of water in the carrier may, for example, range from 1 to 99%, more preferably from 5 to 90%, even more preferably from 35 to 80%, optimally between 40 and 70% by weight of the personal care composition.

Other materials which can be included in the cosmetically acceptable carrier include solvents, humectants, thickeners and powders. Examples of each of these types of material, which can be used singly or as mixtures, are as follows:

Solvents include ethyl alcohol, isopropanol, acetone, ethylene glycol monoethyl ether, diethylene glycol monobutyl ether, diethylene glycol monoethyl ether and mixtures thereof.

Humectants include those of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range, for example, anywhere from 0.5 to 50%, more preferably between 1 and 15% by weight of the composition. Most preferred is glycerol (also known as glycerin). Amounts of glycerin may range, for example, from 0.5% to 50%, more preferably from 1 to 35%, optimally from 2 to 15% by weight of the composition.

A variety of thickening agents may be included in the compositions. Illustrative but not limiting are stearic acid, Acrylamide/Sodium Acryloyldimethyltaurate Copolymer (Aristoflex AVC), Hydroxyethyl Acrylate/Sodium Acryloyldimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range, for example, from 0.05 to 10%, more preferably from 0.3 to 2% by weight of the composition.

Powders include chalk, talc, Fullers earth, kaolin, starch, gums, colloidal silica sodium polyacrylate, tetraalkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

Preferably, the personal care composition has a L&W (line and wrinkle) index of at least −80% and is capable of maintaining the lightness of the skin. More preferably the personal care composition has a L&W index of −70% to 300% and is capable of improving the lightness of the skin by at least 1. Even more preferably, the personal care composition has a L&W index of −45% to 200% and is capable of improving the lightness of the skin by at least 1. The measurements of L&W index is described in Example 2.

The personal care composition of this invention is preferably a skin care composition. More preferably, the composition is preferably an antiperspirant composition or a face (except eye lids and lips) care composition. The skin care composition refers to a composition suitable for topical application to human skin, including leave-on and wash-off products. Preferably the term encompasses a fluid liquid, and particularly a moisturizer rather than a make-up product. Most preferred are leave-on compositions. The term "leave-on" as used with reference to compositions herein means a composition that is applied to or rubbed on the skin, and left thereon. The term "wash-off" as used with reference to compositions herein means a skin cleanser that is applied to or rubbed on the skin and rinsed off substantially immediately subsequent to application. The term "skin" as used herein includes the skin on the face (except eye lids and lips), neck, chest, abdomen, back, arms, under arms, hands, and legs. Preferably "skin" means includes the skin on the face (except eye lids and lips) and under arms. More preferably means skin on the face other than lips and eyelids.

The composition can be formulated in any known format, more preferred formats being creams or lotions.

Packaging for the composition of this invention can be a jar or tube as well as any other format typically seen for cosmetic, cream, washing and lotion type products. The compositions may be applied topically and preferably 1-4 milligrams of composition is applied per square centimeter of skin.

The composition of the invention preferably delivers a cosmetic benefit to the skin of an individual to which it is topically applied. Examples of cosmetic benefits include reducing the appearance of fine lines, wrinkles, pores and/or blemish spots; evening skin tone, or a combination thereof on the desired skin surface.

The following examples are provided to facilitate an understanding of the invention. The examples are not intended to limit the scope of the claims.

EXAMPLES

Material

| Trade name | INCI name | Supplier | Avg. particle size (microns)# | Refractive Index |
|---|---|---|---|---|
| Softtouch* CC6097 | Boron Nitride (tubostratic type) | Momentive | 5 | 2.1/1.8 ($\perp$/∥) |
| SF-6 | Boron Nitride (graphitic) | Merck | 4.5-8.5 | 2.1/1.8 ($\perp$/∥) |
| Optitouch | Ethylene Octene copolymer dispersed in ethylene/ acrylate copolymer | Dow | 1-2.5 | 1.51 |
| EA209 | Ethylene/ Acrylic acid copolymer beads | KOBO | 5-15 | 1.51 |
| CL2080 | Polyethylene | KOBO | 8-14 | 1.51 |
| DC9509 | Vinyl dimethicone/ dimethicone crosspolymer | Dow Corning | 3-5 | 1.41 |

The average particle size of the boron nitride particle is as measured for the aggregated particles using the dynamic light scattering techniques and as reported by the material supplier.
($\perp$/∥) refers to the refractive index as measured with the perpendicular and parallel polarization respectively.

Example A-D, 1-2

Synergistic Effect of Combining Boron Nitride With Non-Silicone Polyolefin Particles A series of skin care compositions were formulated as shown in Table 1.

TABLE 1

| Ingredient | Examples (active wt %) | | | | | |
|---|---|---|---|---|---|---|
| | A | B | 1 | C | 2 | D |
| Water | To 100 | To 100 | To 100 | To 100 | To 100 | To 100 |
| Softtouch*CC6097 | 3.00 | — | 3.00 | — | — | 3.00 |
| Ethylene/Octene co-polymer# | — | 1.00 | 1.00 | — | 1.00 | — |
| SF-6 | — | — | — | 3.00 | 3.00 | — |
| DC9509 | — | — | — | — | — | 1.00 |
| Tween 20 | 2 | 2 | 2 | 2 | 2 | 2 |
| Glycerin | 2 | 2 | 2 | 2 | 2 | 2 |
| VP/VA copolymer | 2.5 | 2.5 | 2.5 | 2.5 | 2.5 | 2.5 |
| Cyclopentasiloxane (D5) | 12 | 12 | 12 | 12 | 12 | 12 |
| Simulgel EG | 3 | 3 | 3 | 3 | 3 | 3 |
| Preservative | 0.5 | 0.5 | 0.5 | 0.5 | 0.5 | 0.5 |

The ethylene octane copolymer used herein was sourced as Optitouch.
(1). Measurement of the gloss degree before and after the personal care compositions is applied.

Wrinkled Bio-skin plates (BP-EW1 #BSC, Beaulax Co., Ltd., Tokyo, Japan) made of polyurethane elastomer were used as substrate to mimic the human skin with wrinkles. A dual-polarized image system called SAMBA (Bossa Nova Technologies, USA) was employed to measure the gloss degree of the wrinkled Bio-skin plates by following the method and principle described by Akira Matsubara [Skin translucency: what is it and how is it measured, The International Federation of Societies of Cosmetic Chemists (IFSCC) Congress 2006, Osaka, Japan]. A software named SAMBA face system (Version 4.3) was equipped for the analysis. The Wrinkled Bio-skin plates were tested against an incident light with exposure time of 80 msec. The operation mode was parallel polarization and crossed polarization modes.

Then, 28 mg of one sample as prepared in Table 1 was applied to and spread by finger cot within a circle of area of 7 cm² area for the gloss test. After waiting for 30 minutes to let the sample dry naturally, the gloss of the wrinkled Bio skin plates was measured again using the SAMBA system.

(2). Calculation of L&W Index

The incident light was reflected and scattered by Bio-skin plates. The specular reflected light kept the same polarization as the incident light whereas the scattering light from the volume (diffused light) was un-polarized. The SAMBA camera acquired successively two images corresponding to two states of polarization (parallel and crossed). The parallel image intensity (P) is contributed from both the reflected and scattered light, and the crossed image intensity (C) is contributed from the scattered light only. The parallel image plus the crossed image is equal to the total image delivered by a traditional camera or perceived by human eye.

The gloss degree was calculated by (P−C)/(P+C). The calculation of gloss degree was performed for each pixel. The standard deviation (STD) of gloss degree is a measure of the uniformity of the skin appearance. The higher the STD the lower is the uniformity. Herein we define a L&W (line and wrinkle) index to demonstrate degree of blurring efficacy of the skin care composition. The L&W index is calculated by (STD of gloss degree before applying sample—STD of gloss degree after applying sample)/(STD of gloss degree before applying sample). The higher the L&W index, the higher is the blurring efficacy of the sample.

(3). Measurement of Color Effect

Bio-skin plate (Color: 50#, ex. BEAULAX, Co. Ltd., Tokyo, Japan) was employed to measure the color. 0.5 g of samples was coated evenly onto Bio-skin plates with area of 250 cm². The coated bio-skin was naturally dried at around 25° C. for 0.5 hours. The L*, a*, and b* of the Bio-skin plate were measured before and after coating of sample by portable spectrophotometer CM2600d (MINOLTA Co. Ltd., Japan) at 6 points. ΔL*, Δa*, Δb* stand for change in whiteness, redness, yellowness after coating of sample compared to prior to coating respectively. E is a consolidated measure of the increase in colour and is calculated using $$\Delta E = \sqrt{\Delta L^2 + \Delta a^2 + \Delta b^2}$$

The data on the the L&W Index is summarized in Table-2.

TABLE 2

| Examples | L&W index |
|---|---|
| A | 0.15% |
| B | −32.28% |
| 1 | 27.61% |
| C | −52.58% |
| 2 | −2.76% |
| D | 19.44% |

Data in Table 2 indicates that composition as per the invention (Exp-1) with turbostratic boron nitride and the claimed polymer exhibits vastly superior blurring efficacy as compared to composition where only one of these ingredients is included (Example A and B). Graphitic boron nitride (Example 2) exhibits lower L&W index than turbostratic boron nitride (Example 1) and combination of turbostratic boron nitride silicone elastomer (Example D), thus it is out of the scope.

Further, efficacy is better when with turbostratic boron nitride as compared to graphitic boron nitride (Example 1 vs. Example 2).

Even further, the efficacy is better when turbostratic boron nitride is combined with non-silicone polyolefin particle (Example 1) as compared to the combination with silicone based polymer particle (Example D).

The data on the color effect is summarized in Table-3.

TABLE 3

| Sample | ΔL* | Δa* | Δb* | ΔE |
|---|---|---|---|---|
| 1 | 5.15 ± 0.464 | −3.74 ± 0.328 | −8.93 ± 0.747 | 10.96 |
| D | 4.22 ± 0.154 | −3.11 ± 0.071 | −7.52 ± 0.173 | 9.16 |

Data in Table 3 indicates that composition as per the invention (Example 1) with turbostratic boron nitride and the claimed polymer exhibits more lightness, less redness and yellowness as compared to composition with turbostratic boron nitride and silicone based polymer particle (Example D), as desired for skin lightening benefit.

Example 1, A, E-H

Compositions When Polyolefin Particles Outside the Claimed Size Range Are Used

Compositions as shown in Table-4 were prepared. Compositions 1 and A are repeated here for comparison.

TABLE 4

| Ingredient | Examples | | | | | |
|---|---|---|---|---|---|---|
| (active wt %) | 1 | A | E | F | G | H |
| Water | To 100 | To 100 | To 100 | To 100 | To 100 | To 100 |
| Softtouch*CC6097 | 3.00 | 3.00 | — | 3.00 | — | 3.00 |
| Optitouch | 1.00 | — | — | — | — | — |
| EA-209 | — | — | 1.00 | 1.00 | — | — |
| CL2080 | — | — | — | — | 1.00 | 1.00 |
| Tween 20 | 2 | 2 | 2 | 2 | 2 | 2 |
| Glycerin | 2 | 2 | 2 | 2 | 2 | 2 |
| VP/VA copolymer | 2.5 | 2.5 | 2.5 | 2.5 | 2.5 | 2.5 |
| Cyclopentasiloxane (D5) | 12 | 12 | 12 | 12 | 12 | 12 |
| Simulgel EG | 3 | 3 | 3 | 3 | 3 | 3 |
| Preservative | 0.5 | 0.5 | 0.5 | 0.5 | 0.5 | 0.5 |

The L&W index of the various compositions in Table-4 were measured and the values are summarized in Table-5.

TABLE 5

| Example | L&W index |
|---|---|
| 1 | 27.61% |
| A | 0.15% |
| E | −67.02% |
| F | 4.95% |
| G | −67.91% |
| H | −8.13% |

The data in Table-5 indicates that the efficacy obtained with composition comprising the polyolefin of the claimed particles size (Example 1) is superior to samples prepared with particles outside the claimed sizes (Example F and H).

The invention claimed is:

1. A personal care composition comprising:
   a) turbostratic boron nitride particles;
   b) non-silicone polyolefin particles having an average particle size in the range of 0.5 to 5 microns; and
   c) a cosmetically acceptable carrier.

2. The composition as claimed in claim 1, wherein said boron nitride particles have an average particle size in the range of about 100 nm to about 10 microns.

3. The composition as claimed in claim 1, wherein said boron nitride particles are present in amount of about 0.1 to about 15% by weight of the composition.

4. The composition as claimed in claim 1, wherein said non-silicone polyolefin particles have a $d_{10}$ value higher than about 1.1 μm and a $d_{90}$ value lower than about 3.3 μm.

5. The composition as claimed in claim 1, wherein said non-silicone polyolefin particles comprise homo or co-polymers of hydrocarbon olefin having 2 to 10 carbon atoms.

6. The composition as claimed in claim 5, wherein said hydrocarbon olefin does not comprise an oxygen, a silicon or a nitrogen atom.

7. The composition as claimed in claim 1, wherein said olefin comprises ethylene, propylene, octene or combinations thereof.

8. The composition as claimed in claim 1, wherein said non-silicone polyolefin particles comprise ethylene/octane copolymer.

9. The composition as claimed in claim 1, wherein said non-silicone polyolefin particles have a refractive index in the range of about 1.4 to about 1.6.

10. The composition as claimed in claim 1, wherein said non-silicone polyolefin particles are present in amount of 0.1 to 10% by weight of the composition.

11. The composition as claimed in claim 1, wherein said cosmetically acceptable carrier comprises an oil-in-water emulsion.

12. A method of improving the appearance of skin by providing improved blurring and reduced shine comprising the step of applying the composition as claimed in claim 1 on the desired skin surface.

* * * * *